United States Patent [19]

Sperling et al.

[11] Patent Number: 4,709,109
[45] Date of Patent: Nov. 24, 1987

[54] PREPARATION OF ALKENYLAROMATICS

[75] Inventors: Karin Sperling, Wachenheim; Martin Fischer, Ludwigshafen, both of Fed. Rep. of Germany

[73] Assignee: BASF Aktiengesellschaft, Ludwigshafen, Fed. Rep. of Germany

[21] Appl. No.: 917,906

[22] Filed: Oct. 10, 1986

[30] Foreign Application Priority Data

Oct. 17, 1985 [DE] Fed. Rep. of Germany ....... 3536929

[51] Int. Cl.$^4$ ............................................. C07C 15/46
[52] U.S. Cl. ................................... 585/438; 585/428; 585/429; 585/452; 585/453
[58] Field of Search ............... 585/438, 452, 453, 428, 585/429

[56] References Cited

U.S. PATENT DOCUMENTS 3,641,176  2/1972  Jenkins et al. .
4,054,612 10/1977  Yagi et al. ............................ 585/429

OTHER PUBLICATIONS

C. Dixon, E. W. Duck, and D. K. Jenkins, Organometal. Chem. Synthesis 1 (1970/1971), 1, pp. 77–86.

Primary Examiner—Curtis R. Davis
Attorney, Agent, or Firm—John H. Shurtleff

[57] ABSTRACT

Alkenylaromatics I

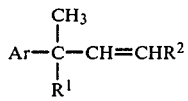

where $R^1$ is $C_1$–$C_6$-alkyl, $R^2$ is H or $C_1$–$C_{10}$-alkyl and Ar is aryl, are prepared by reacting a vinylaromatic II

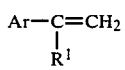

with an α-olefin III

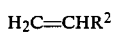

in the presence of a nickel-containing catalyst system consisting of (a) a nickel(II) salt of a carboxylic acid, of an alcoholate or of a phenolate, (b) a phosphite or phosphine and (c) an organoaluminum compound V

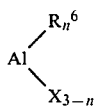

where $R^6$ is $C_1$–$C_{12}$-alkyl, X is halogen and n is 1 or 2, or a mixture of compounds V.

15 Claims, No Drawings

PREPARATION OF ALKENYLAROMATICS

The present invention relates to an improved process for the preparation of alkenylaromatics of the formula I $$Ar-\underset{\underset{R^1}{|}}{\overset{\overset{CH_3}{|}}{C}}-CH=CHR^2 \qquad I$$

where $R^1$ is alkyl of 1 to 6 carbon atoms, $R^2$ is hydrogen or alkyl of 1 to 10 carbon atoms and Ar is a substituted or unsubstituted aryl, by reacting a vinylaromatic of the formula II $$Ar-\underset{\underset{R^1}{|}}{C}=CH_2 \qquad II$$

with an α-olefin of the formula III $$H_2C=CHR^2 \qquad III$$

in the presnece of a nickel-containing catalyst system.

It is known that vinylaromatics can be combined with ethylene to form alkenylaromatics using a catalyst system consisting of Ni(PCl$_3$)$_4$, AlBr$_3$ and butyllithium in a molar ratio of 0.25:5.0:7.5 in cyclohexane/hexane at from 15° to 42° C. (disclosed in, for example, German Laid-Open Application DOS No. 1,792,571 or C. Dixon, E. W. Duck, and D. K. Jenkins, Organometal. Chem. Synth. 1 (1970/71) 1, 77–86). The disadvantages of this process are the expensive synthesis of the nickel complex Ni(PCl$_3$)$_4$, the use of expensive butyllithium in a 30-fold excess for the preparation of the catalyst, and the low yield of about 63%.

Furthermore, the reaction of styrene and α-methylstyrene with ethylene in the presence of nickel diacetylacetonate, triphenyl phosphite, triethylaluminum and BF$_3$.Et$_2$O in a molar ratio of 1:1:3:5 at 25° C. with yields of about 97% is described in Azerb. Khim. Zh. 1978 (2), 3–8. However, this process has the disadvantage that the catalyst has to be produced in the presence of a fifth component, ie. butadiene, at a very low temperature of −78° C., and binding of the olefins has to be carried out under superatmospheric pressure in an autoclave. To obtain good results, the boron trifluoride component has to be used in a large excess.

It is an object of the present invention to provide a better nickel-containing catalyst system for the reaction of vinylaromatics with α-olefins to give alkenylaromatics, which are important starting materials for the preparation of, for example, alkylaromatics and anthraquinone derivatives. The catalyst system should be very simply and cheaply obtainable and should permit a high conversion coupled with high selectivity under mild reaction conditions.

We have found that this object is achieved, and that alkenylaromatics of the formula I $$Ar-\underset{\underset{R^1}{|}}{\overset{\overset{CH_3}{|}}{C}}-CH=CHR^2 \qquad I$$

where $R^1$ is alkyl of 1 to 6 carbon atoms, $R^2$ is hydrogen or alkyl of 1 to 10 carbon atoms and Ar is unsubstituted or substituted aryl, can be particularly advantageously prepared by reacting a vinylaromatic of the formula II $$Ar-\underset{\underset{R^1}{|}}{C}=CH_2 \qquad II$$

with an α-olefin of the formula III $$H_2C=CHR^2 \qquad III$$

in the presence of a nickel-containing catalyst system, if the catalyst system used is prepared by mixing (a) an Ni(II) salt of a carboxylic acid, of an alcoholate and/or of a phenolate, (b) a trivalent organic phosphorus compound of the formula IV $$P\begin{matrix} \diagup (O)_a-R^3 \\ -(O)_b-R^4 \\ \diagdown (O)_c-R^5 \end{matrix} \qquad IV$$

where $R^3$, $R^4$ and $R^5$ are each alkyl, cycloalkyl, aryl or aralkyl and the indices a, b and c are each zero or 1, and (c) an organoaluminum compound of the formula V $$Al\begin{matrix} \diagup R_n^6 \\ \diagdown X_{3-n} \end{matrix} \qquad V$$

where the radicals $R^6$ are identical or different alkyl groups of 1 to 12 carbon atoms, X is halogen and n is 1 or 2, or a mixture of two compounds of the formula V, the molar ratio of nickel to phosphorus being from 1:0.5 to 1:10 and that of nickel to aluminum being from 1:1 to 1:20.

Where α-methylstyrene and ethylene are used as starting materials, the reaction is described by the following equation:

$$\underset{\underset{CH_2}{\|}}{\underset{C}{C_6H_5 \diagdown \diagup CH_3}} + H_2C=CH_2 \xrightarrow{Ni-catalyst}$$

$$H_5C_6-\underset{\underset{CH_3}{|}}{\overset{\overset{CH_3}{|}}{C}}-CH=CH_2$$

Suitable starting materials II are vinylaromatics in which $R^1$ is alkyl of 1 to 6, preferably 1 to 4, in particular 1 or 2, carbon atoms, eg. methyl, ethyl, n-propyl, isopropyl, n-butyl, isobutyl, n-pentyl, isopentyl or hexyl. α-Methyl- and α-ethylstyrenes are particularly suitable.

Aryl is, for example, phenyl or naphthyl, which may furthermore carry substituents which are inert under the reaction conditions, such as alkyl or alkoxy radicals of 1 to 6, in particular 1 to 4, carbon atoms, eg. methyl, ethyl, propyl, isopropyl, butyl, isobutyl or tert-butyl, or the corresponding alkoxy radicals or halogen, such as fluorine, chlorine, bromine or iodine.

Examples of starting materials II are α-methylstryene, α-ethylstyrene, α-n-propylstyrene, α-n-butylstyrene, p-methyl- and p-methoxy-α-methylstyrene, p-ethyl-, p-isopropyl- and p-tert-butyl- α-methylstyrene, p-bromo- and p-chloro-α-methylstyrene and the corresponding o- and m-substituted α-methylstyrenes, as well as p-ethyl- and p-methyl-α-ethylstyrene and 1-isopropylenenaphthalene.

α-Olefins of the formula III are those in which $R^2$ is hydrogen or alkyl of 1 to 10, in particular 1 to 6, preferably 1 to 4, carbon atoms, for example ethene, propene, but-1-ene, pent-1-ene, hex-1-ene, hept-1-ene, oct-1-ene, non-1-ene, dec-1-ene, neohexene, 3-methyl-but-1-ene, 4-methylpent-1-ene, 6-ethylhept-1-ene or 4-tert-butyl-hept-1-ene.

The starting materials II are used with the starting materials III in general in a stoichiometric amount or in excess, preferably in an amount of from 1 to 2, in particular from 1 to 1.5 moles of starting material III per mole of starting material II.

The nickel-containing catalyst system can be prepared by mixing a nickel(II) salt of carboxylic acid, of an alcoholate of a saturated aliphatic alcohol or a phenolate with (a) a phosphite or phosphine and (b) an organoaluminum compound V.

Examples of nickel(II) salts of alcoholates or phenolates are $Ni(O-CH_3)_2$, $Ni(O-C_2H_5)_2$, $Ni(O-i-C_3H_7)_2$, $Ni(O-C_4H_9)_2$, $Ni(O-tert.-C_4H_9)_2$ and $Ni(O-C_6H_5)_2$. The stated organic groups may furthermore carry substituents which are inert under the reaction conditions, such as low molecular weight alkyl or alkoxy groups. Nickel (II) salts of the formula VI $$Ni(OOCR^7)(OOCR^8) \qquad (VI)$$

where $R^7$ and $R^8$ are identical or different and are each an aliphatic, araliphatic or aromatic radical, for example alkyl, haloalkyl, alkenyl, cycloalkyl, aryl, aralkyl or alkenyl are particularly preferred for the preparation of the novel catalyst system. The number of carbon atoms in the organic radicals is only of importance for achieving good solubility of the nickel salts in the solvent used. For example, the salts of long-chain carboxylic acids in which $R^7$ and $R^8$ together are of 5 to 25 carbon atoms are preferably used in nonpolar solvents. The mixed nickel salts described in European Pat. No. 24,971 and in which $R^7$ is an unsubstituted or substituted hydrocarbon radical of not less than 5 carbon atoms and $R^8$ is haloalkyl of 1 to 3 carbon atoms, eg. trifluoromethyl or trichloromethyl, are preferably employed.

For example, the nickel(II) salts of the following carboxylic acids may be used, individually or as a mixture with one another: acetic acid, phenylacetic acid, chloroacetic acid, trifluoro-, trichloro-, tribromo- and triiodoacetic acid, propionic acid, 2-chloropropionic acid, butyric acid, isobutyric acid, n-valeric acid, 4-methylvaleric acid, caproic acid, 2-ethylhexanecarboxylic acid, enanthic acid, caprylic acid, capric acid, lauric acid, myristic acid, palmitic acid, stearic acid, oleic acid, cyclohexanecarboxylic acid, benzoic acid, p-chlorobenzoic acid and m-toluic acid. The stated carboxylic acids may furthermore carry groups which are inert under the reaction conditions, such as alkyl or alkoxy of 1 to 4 carbon atoms or halogen. Nickel(II) salts of dicarboxylic acids can also be used as catalyst components.

Suitable trivalent organic phosphorus compounds are tertiary phosphines or tertiary phosphites of the formula IV

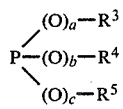
$$\text{IV}$$

where $R^3$, $R^4$ and $R^5$ are identical or different and are each alkyl, such as methyl, ethyl, propyl, isopropyl, butyl, tert-butyl or octyl, cycloalkyl, such as cyclohexyl, aralkyl, such as benzyl, or aryl such as phenyl or toluyl. Typical examples of such phosphorus compounds are: $P(CH_3)_3$, $P(C_2H_5)_3$, $P(n-C_3H_7)_3$, $P(n-C_4H_9)_3$, $P(tert.-C_4H_9)_3$ $P(C_8H_{17})_3$, $P(C_6H_{11})_3$, $P(C_6H_5)_3$, $P(CH_2C_6H_5)_3$, $P(C_2H_5)_2(C_6H_5)$, $P(C_2H_5)-(C_6H_5)_2$, $P(OCH_3)_3$, $P(O-C_2H_5)_3$, $P(O-n-C_3H_7)_3$, $P(O-i-C_3H_7)_3$, $P(O-n-C_4H_9)_3$, $P(O-C_6H_5)_3$, $P(O-CH_2C_6H_5)_3$ and $P(OCH_3)(C_6H_5)_2$.

Particularly suitable organoaluminum compounds V

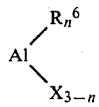
$$\text{V}$$

are those in which the radicals $R^6$ are identical or different alkyl groups of 1 to 12, preferably 1 to 6, in particular 1 to 4, carbon atoms, eg. methyl, ethyl, n-propyl, isopropyl, n-butyl or isobutyl, X is fluorine, chlorine, bromine or iodine and n is 1 or 2, or mixtures of two different compounds of the formula V.

The following compounds are examples: methylaluminum dichloride and dibromide, ethylaluminum dichloride and dibromide, isopropylaluminum dibromide, n-butylaluminum dichloride, dimethylaluminum chloride and diethylaluminum chloride and bromide. An example of a mixture of these compounds is ethylaluminum sesquichloride. Mixtures of an akylaluminum dichloride and a dialkylaluminum chloride in a molar ratio of, for example, from 20:1 to 2:1, in particular from 10:1 to 5:1, are preferably used.

The catalyst can be prepared by mixing the nickel(II) salt in a solvent with the trivalent organic phosphorus compound and the organoaluminum compound at from $-20°$ to $+80°$ C., in particular at room temperature, preferably under an inert gas, such as nitrogen or argon. Preferably, the nickel salt is first mixed with the phosphorus compound, and the organoaluminum compound is then added. This gives a solution of catalyst which can be used directly for the reaction.

Solvents which can advantageously be used for preparing the catalyst are aromatic hydrocarbons, such as toluene, benzene, ethylbenzene or o-, m- or p-xylene, aliphatic hydrocarbons, such as pentane, hexane, heptane, nonane or petroleum ether, cycloaliphatic hydrocarbons, such as cyclohexane, and halohydrocarbons, such as chlorobenzene or methylene chloride as well as mixtures of these.

The amount of solvent is not critical. The solvent is generally used in an amount sufficient to dissolve the catalyst and to give a readily stirrable mixture after the addition of the reactants II and III. In order to keep the amount of solvent as low as possible, it may be advantageous if some of the crude reaction mixture obtained after the reaction is reused as a reaction medium for the catalyst preparation and subsequent reaction.

The mode of action of the catalyst system is not known exactly. High catalytic activity is found in particular when the molar ratio of nickel to phosphorus is from 1:0.5 to 1:10, preferably from 1:1 to 1:3, and the molar ratio of nickel to aluminum is from 1:1 to 1:20, preferably from 1:3 to 1:10.

In general, small amounts of the catalyst are sufficient to ensure a high conversion and a high selectivity in the reaction of II with III. As a rule, the amount of catalyst system corresponds to 0.01–0.0001, in particular 0.001–0.0002, mol % of nickel per mole of II.

The process according to the invention can be carried out, for example, as follows: the starting materials II and III are added at about the same time to the catalyst system consisting of the nickel(II) salt VI, the organic phosphorus compound IV and the organoaluminum compound V in a solvent or dissolved in some of the reaction mixture obtained from a previous reaction.

Both the preparation of the catalyst and the catalytic reaction are preferably carried out in an inert gas atmosphere, substantially in the absence of water. Examples of suitable inert gases are nitrogen, argon and helium. The reaction temperature is generally from 0° to 80° C., in particular from 30° to 45° C. The reaction according to the invention can be carried out continuously or batchwise by a conventional technique, under atmospheric or slightly superatmospheric pressure of about 1–6 bar.

The crude reaction mixture is worked up in a conventional manner by isolating the reaction products and any starting materials present from the mixture by distillation, if necessary after the catalyst has been decomposed, for example with an aqueous solution.

The alkenylaromatics which are obtained in a high yield by the process according to the invention and possess an allyl double bond are useful intermediates for the preparation of alkylaromatics, alkylanthraquinones, dyes, scents or polymers, and are difficult to obtain by other routes.

EXAMPLE 1

50 ml of dry toluene, 1.2 ml (2 millimoles) of a solution of nickel trifluoroacetate ethylhexanoate in toluene (1.7 molar) and 0.6 ml (2.3 millimoles) of triphenyl phosphite were initially taken under nitrogen. 8.0 ml (10 millimoles) of a 20.8% strength solution of ethylaluminum dichloride in hexane were then added dropwise at room temperature. 472 g (4 moles) of α-methylstyrene and ethylene gas were then added to this catalyst solution in the course of 4 hours, the gas stream being adjusted so that hardly any waste gas escaped. The ethylene consumption was about 20 l/h. The temperature was kept at from 35° to 40° C. by cooling with water. The reaction mixture was then stirred for 1 hour while ethylene was passed in at the stated temperature.

Composition of the reaction mixture:
3-methyl-3-phenylbut-1-ene: 83.3% by weight
α-methylstyrene: 3.6% by weight About 2% of butene and 3% of cotrimers of 1 molecule of α-methylstyrene and 2 molecules of ethylene were obtained as byproducts (eg. 5-methyl-5-phenylhex-2-ene and isomers). The conversion based on α-methylstyrene was 95%, and the selectivity based on 3-methyl-3-phenylbut-1-ene was 91%.

EXAMPLE 2

The procedure described in Example 1 was followed, except that 50 g of a reaction mixture obtained as described in Example 1 were used as the solvent and 1.2 ml (2 millimoles) of nickel trifluoroacetate ethylhexanoate, 0.6 ml (2.3 millimoles) of triphenyl phosphite and 8.0 ml (12 millimoles) of ethylaluminum dichloride (25% strength in hexane) were employed as the catalyst system. 236 g (2 moles) of α-methylstyrene and ethylene gas were added in the course of 3 hours, after which the mixture was stirred for a further hour while ethylene was passed in.

Composition of the reaction mixture:
3-methyl-3-phenylbut-1-ene: 87.7% by weight
α-methylstyrene: 5.25% by weight
conversion: 92%
selectivity: 97%

EXAMPLE 3

The procedure described in Example 1 was followed, except that 50 g of a reaction mixture obtained as described din Example 1 was used as the solvent and 1.21 ml (2.2 millimoles) of nickel di(ethylhexanoate) (10% strength in toluene), 0.66 ml (2.8 millimoles) of triphenyl phosphite and 8.8 ml (13.2 millimoles) of ethylaluminum dichloride (25% strength in hexane) were employed as the catalyst system. 236 g (2 moles) of α-methylstyrene and ethylene gas were added in the course of 2 hours, after which the mixture was stirred for a further hour while ethylene was passed in.

Composition of the reaction mixture:
3-methyl-3-phenylbut-1-ene: 90.7% by weight
α-methylstyrene: 1.3% by weight
conversion: 98%
selectivity: 98%

EXAMPLE 4

The procedure described in Example 1 was followed except that, instead of ethylene, propene was reacted with 236 g (2 moles) of α-methylstyrene. 1.2 ml (2 millimoles) of nickel trifluoroacetate ethylhexanoate, 0.6 ml (2.3 millimoles) of triphenyl phosphite and 18 ml (20 millimoles) of ethylaluminum dichloride (in hexane) in 400 ml of dry toluene were used as the catalyst solution.

Composition of the reaction mixture:
4-methyl-4-phenylpent-1ene: 88% by weight
α-methylstyrene: 7.8% by weight
conversion: 92.5%
selectivity: 91%

EXAMPLE 5

The precedure described in Example 1 was followed, except that 50 ml of absolute $CH_2Cl_2$, as the solvent, 1.32 ml (2.75 millimoles) of nickel trifluoroacetate ethylhexanoate, 0.55 ml (2.8 millimoles) of triphenyl phosphite and 10.3 ml (15.4 millimoles) of ethylaluminum dichloride (25% strength in hexane) were employed.

236 g (2 moles) of α-methylstyrene and ethylene gas were added in the course of 3 hours, after which the mixture was stirred for a further hour while ethylene was passed in.

Composition of the reaction mixture:
3-methyl-3-phenylbut-1-ene: 53% by weight
α-methylstyrene: 0.98% by weight
conversion: 98%
selectivity: 59%

EXAMPLE 6

The procedure described in Example 1, using 50 ml of toluene, was followed, except that 0.55 ml (1 millimole) of nickel di-(ethylhexanoate) (10% strength in toluene), 0.3 ml (1.3 millimoles) of triphenyl phosphite and 4.77 ml (6.6 millimoles) of a 10:1 mixture of EtAlCl$_2$ and Et$_2$AlCl in hexane were employed as the catalyst system. 236 g (2 moles) of α-methylstyrene and ethylene gas were added in the course of 2 hours, after which the mixture was stirred for a further hour while ethylene was passed in.

Composition of the reaction mixture:
3-methyl-3-phenylbut-1-ene: 86.3% by weight
α-methylstyrene: 7.4% by weight
conversion: 90%
selectivity: 97%

EXAMPLE 7

The procedure described in Example 1, using 50 ml of toluene, was followed, except that 0.24 g (0.44 millimole) of nickel di(ethylhexanoate) (10% strength in toluene), 0.15 g (0.57 millimole) of triphenylphosphine, 2 ml (2 millimoles) of a 1 molar solution of Et$_2$AlCl in hexane and 1.4 ml (2 millimoles) of 25% strength solution of EtAlCl$_2$ in hexane were employed as the catalyst system.

236 g (2 moles) of α-methylstyrene and ethylene gas were added in the course of 2 hours, after which the mixture was stirred for about a further hour while ethylene was passed in.

Composition of the reaction mixture:
3-methyl-3-phenylbut-1-ene: 39% by weight
α-methylstyrene: 30.75% by weight
conversion: 54%
selectivity: 87%

EXAMPLE 8

The procedure described in Example 1, using 50 ml of absolute toluene, was followed, except that 0.29 g (0.5 millimole) of nickel di(ethylhexanoate), 0.40 g (1.3 millimoles) of triphenyl phosphite, 4.2 ml (6 millimoles) of EtAlCl$_2$ (25% strength in hexane) and 1.2 ml (1.2 millimoles) of Et$_2$AlCl (1 molar in hexane) were employed as the catalyst system.

264 g (2 moles) of p-methyl-α-methylstyrene were added dropwise in the course of 4 hours while ethylene was passed in, after which the mixture was stirred for a further hour while ethylene gas was fed in.

Composition of the reaction mixture:
3-methyl-3-(p-methylphenyl)-but-1-ene: 84.4% by weight
p-methyl-α-methylstyrene:
conversion: 100%
selectivity: 91%

The composition of the reaction mixture was determined by gas chromatography in all examples.

We claim:

1. A process for the preparation of an alkenylaromatic of the formula I

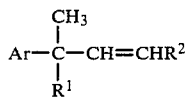

where R$^1$ is alkyl of 1 to 6 carbon atoms, R$^2$ is hydrogen or alkyl of 1 to 10 carbon atoms and Ar is unsubstituted or substituted aryl, by reacting a vinylaromatic of the formula II

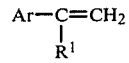

with an α-olefin of the formula III $$H_2C=CHR^2 \qquad III$$

in the presence of a nickel-containing catalyst system, wherein the improvement comprises using a catalyst system prepared by mixing
(a) an Ni (II) salt of a carboxylic acid, of an alcoholate and/or a phenolate,
(b) a trivalent organic phosphorus compound of the formula IV

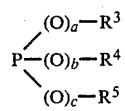

where R$^3$, R$^4$ and R$^5$ are each alkyl, cycloalkyl, aryl or aralkyl and the indices a, b and c are each zero or 1, and
(c) an organoaluminum compound of the formula V

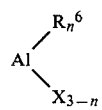

where the radicals R$^6$ are identical or different alkyl groups of 1 to 12 carbon atoms, X is halogen and n is 1 or 2, or a mixture of two compounds of the formula V, the molar ratio of nickel to phosphorus being from 1:0.5 to 1:10 and that of nickel to aluminum being from 1:1 to 1:20.

2. A process as claimed in claim 1, using a nickel(II) salt of the formula VI $$Ni(OOCR^7)(OOCR^8) \qquad VI$$

where R$^7$ and R$^8$ are identical or different and are each alkyl, haloalkyl, cycloalkyl, alkenyl, aryl, aralkyl or alkaryl.

3. A process as claimed in claim 2, wherein R$^7$ is a hydrocarbon radical of 5 to 20 carbon atoms and R$^8$ is a halogen-substituted alkyl radical of 1 to 3 carbon atoms.

4. A process as claimed in claim 1, wherein a phosphite is used as the organophosphorus compound.

5. A process as claimed in claim 1, wherein the amount of the catalyst system corresponds to 0.01–0.0001 mol % of nickel per mole of II.

6. A process as claimed in claim 1, wherein the catalyst is prepared by mixing (a) the nickel(II) salt in a solvent with (b) the trivalent organic phosphorus compound and (c) the organoaluminum compound at from −20° to +80° C., using an amount of solvent sufficient to dissolve the catalyst components.

7. A process as claimed in claim 6, wherein the solvent is selected from the group consisting of aromatic hydrocarbons, aliphatic hydrocarbons, cycloaliphatic hydrocarbons, halohydrocarbons and mixtures thereof.

8. A process as claimed in claim 1, wherein the molar ratio of nickel to phosphorous is 1:1 to 1:3, and the molar ratio of nickel to aluminum is from 1:3 to 1:10.

9. A process as claimed in claim 1, wherein the amount of the catalyst system corresponds to 0.001 to 0.0002 mol% of nickel per mole of II.

10. A process as claimed in claim 1, wherein the vinylaromatic reactant II is selected from the group consisting of α-methylstyrene, α-ethylstyrene, α-n-propylstyrene, α-n-butylstyrene, p-methyl and p-methoxy-α-methylstyrene, p-ethyl-, p-isopropyl- and p-tert-butyl-α-methylstyrene, p-bromo- and p-chloro-α-methylstyrene and the corresponding o- and m-substituted α-methylstyrenes, p-ethyl- and p-methyl-α-ethylstyrene and 1-isopropylene-naphthalene, and wherein the α-olefin reactant III is selected from the group consisting of ethene, propene, but-1-ene, pent-1-ene, hex-1-ene, hept-1-ene, oct-1-ene, non-1-ene, dec-1-ene, neohexene, 3-methyl-but-1-ene, 4-methylpent-1-ene, 6-ethylhept-1-ene and 4-tert-butylhept-1-ene.

11. A process as claimed in claim 1, wherein the reactant II is α-methylstyrene.

12. A process as claimed in claim 11, wherein reactant III is selected from the group consisting of ethene and propene.

13. A process as claimed in claim 1, wherein reactant II is p-methyl-α-methylstyrene.

14. A process as claimed in claim 13, wherein reactant III is ethene.

15. A process as claimed in claim 6, wherein the preparation of the catalyst system and the catalytic reaction are carried out in an inert gas atmosphere, substantially in the absence of water.

* * * * *